United States Patent [19]
Hüschelrath

[11] Patent Number: 4,763,070
[45] Date of Patent: Aug. 9, 1988

[54] METHOD AND APPARATUS TO COMPENSATE FOR LATERAL CHANGES OF A FERROMAGNETIC BODY DURING MAGNETIC TESTING

[75] Inventor: Gerhard Hüschelrath, Laufach, Fed. Rep. of Germany

[73] Assignee: NUKEM GmbH, Hanau, Fed. Rep. of Germany

[21] Appl. No.: 778,515

[22] Filed: Sep. 20, 1985

[30] Foreign Application Priority Data

Sep. 27, 1984 [DE] Fed. Rep. of Germany ....... 3435442

[51] Int. Cl.⁴ ..................... G01N 27/72; G01N 27/82; G01R 33/12
[52] U.S. Cl. ..................................... 324/225; 324/242
[58] Field of Search .......................... 324/225, 239–243

[56] References Cited

U.S. PATENT DOCUMENTS 4,383,218  5/1983  Hansen et al. ...................... 324/225
4,538,108  8/1985  Huschelrath et al. .............. 324/232

FOREIGN PATENT DOCUMENTS

2142351  9/1978  Fed. Rep. of Germany .
2843570  4/1979  Fed. Rep. of Germany .
2906436  8/1980  Fed. Rep. of Germany .
3132808  3/1983  Fed. Rep. of Germany .
1567166  4/1980  United Kingdom .

Primary Examiner—Reinhard J. Eisenzopf
Assistant Examiner—Walter E. Snow
Attorney, Agent, or Firm—Cushman, Darby & Cushman

[57] ABSTRACT

A method and a device for non-destructive testing of ferro-magnetic bodies for structural faults by means of magnetization. The structural faults cause changes in the magnetic field which are picked up by stationary magnetic field detectors arranged close to the surface of the body, which are arranged perpendicular to the direction of magnetization of the body. The outputs of the magnetic field detectors are connected in a time-division multiplex manner to an evaluation unit. Predetermined positions of the magnetic field detectors are assigned compensation values in relation to the position of the respective weld, the compensation values being subtracted with the correct sign from the measured values produced by the magnetic field detectors. The corrected measured values obtained in this manner are subjected to a threshold value test to determine if structural faults are present. Furthermore, a lateral deviation of the weld from its original position is monitored. The compensation values are reassigned in accordance with the actual position of the weld with regard to the magnetic field detectors before the values are offset once more against the measured values.

8 Claims, 4 Drawing Sheets

METHOD AND APPARATUS TO COMPENSATE FOR LATERAL CHANGES OF A FERROMAGNETIC BODY DURING MAGNETIC TESTING

BACKGROUND OF THE INVENTION

The present invention relates to a testing arrangement for non-destructive testing of ferro-magnetic bodies for structural defects by means of magnetizing the bodies in which the structural defects cause changes in the magnetic field pattern, the changes being picked up by stationary magnetic field detectors arranged on or near the surface of the bodies, the detectors being arranged along the periphery of the bodies and having outputs connected in a specified sequence and in a time-division multiplex manner to an evaluation circuit.

In the prior art, when welded pipes of ferritic material are tested, the lines of weld cause stray fluxes which limit the error tracing capability of systems with rotating magnetic fields. In the case of lines of weld extending in the longitudinal direction of the pipe, the magnetic field probes are arranged in differential connection. The magnetic field probes also extend along the longitudinal axis of the pipe. The measured values outputted by the magnetic field probes are weighted differently because of the lines of weld. A disadvantage here, however, is that long longitudinal errors can only be recognized in the entrance and exit area of the testing arrangement.

SUMMARY OF THE INVENTION

It is an object of the present invention to achieve high precision in error location on bodies with lines of weld even on those with errors extending in the longitudinal axis direction of the bodies.

This object and other objects according to the present invention are achieved by a method for non-destructive testing of the ferromagnetic bodies for structural defects by means of magnetizing the bodies in which the structural defects cause changes in the magnetic field pattern, the changes being picked up by stationary magnetic field detectors arranged on or near the surface of the bodies, the detectors being arranged along the periphery of the bodies and having outputs connected in a specified sequence and in a time-division multiplex manner to an evaluation circuit. The method according to the present invention also provides for measurement of a test specimen for structural defects, such that compensation values assigned to the specified positions of the magnetic field detectors in relation to the appropriate weld are subtracted with the correct sign from the measured values outputted by the magnetic field detectors for compensation. The correspondingly corrected measured values are then checked with threshold values determinable in advance for the presence of structural defects. A minimum measured value is understood to be a value of zero or approximately zero. At the same time, the lateral changes in the positions of the magnetic field detectors with regard to the weld are continuously monitored, and the compensation values are reassigned with the measured values in accordance with the actual position of the magnetic field detector concerned in relation to the weld. Thus, according to the present invention the detrimental effects on measuring accuracy caused by the welds can be compensated for particularly well.

The present invention is based on the fact that stationary magnetic field sensors whose positions do not change with respect to the weld of the body when the body is longitudinally shifted are particularly suitable for the assignment of compensation values. The compensation values are matched to the stray fluxes generated by the respective weld on the surface vertical to the longitudinal direction including those areas of the body adjacent to the weld on both sides. The stray fluxes are measured on a test specimen and stored for later processing along with the body to be tested for errors. It is also possible to determine in advance stray fluxes typical for the weld on a fault-free section of a body to be tested and on this basis to stipulate the compensation values for suppressing the influence of the weld on the measured values evaluated for error tracing.

Also according to the present invention, corrective measures are taken that ensure that the influence of the stray fluxes caused by the weld can also be compensated when the body makes lateral movements in addition to its movement in the longitudinal direction. Lateral movement of the body during conveying in the longitudinal direction, particularly with round cross-sections and long bodies, cannot in practice be avoided completely without unacceptable expense being involved for the guidance means of the body. A lateral movement of this nature by the body is taken into account in the method of the present invention by a selection of the compensation values that are altered corresponding to the shift.

A preferred embodiment of the present invention is characterized in that the measured values generated by the magnetic field detectors are stored for monitoring lateral changes in the positions of the magnetic field detectors in relation to the weld. Also the first corrected measured values are generated by correct-signed subtraction and are checked both for overstepping the threshold values and for the correct sign. The compensation values for the respective magnetic field detectors are set to the compensation value of the adjacent magnetic field detector in the event of the threshold values being exceeded as a function of sign changes of the first corrected measured values, and second corrected measured values are obtained by correct-signed subtraction using the reassigned compensation values, the second measured values being compared with the first corrected measured values. The steps are then repeated with reassigned compensation values of the adjacent magnetic field detectors in the case of second corrected measured values that are lower than the first corrected measured values until the corrected values are greater than the measured values obtained in the previous step. The assignment of the compensation values to the lowest corrected measuring values received is the starting basis for further compensation, and the lowest corrected measuring values received are checked as to whether they exceed the threshold values, and errors are signalled when the threshold values are exceeded.

According to a feature of the invention the "weld" compensation values are shifted to obtain a corrected measured value of zero for the magnetic field detectors if the pattern of the compensation values matches the pattern of the measured values. Deviations in the pattern generate a corrected measured value that is greater or smaller than zero, but which is always a minimum value for the correct-position assignment of the compensation values. An error signal that is included in the set of measured values only affects the deviation of the minimum from the zero value, and if the minimum exceeds the respective threshold value, there is an error in the structure. To simplify location of the minimum, it is determined depending on the direction and using the shifting device, the minimum is determined by passing over it once. If the corrected measured values reach the noise threshold, no further assignment of adjacent compensation values is necessary since the noise threshold represents the absolute minimum. Changes in the position of the weld during the longitudinal shift of the respective body to be tested have the effect in this method of reassigning the compensation values by shifting the values in the cells of the first memory. The position changes between the weld and the magnetic field detectors are thus determined with the same means as for structural defects. The only difference is in the sequence that the means are used for position changes and structural defects. This reduces the expense of the test substantially.

According to a further feature of the invention, the measured values corrected with the greatest compensation values are stored at every reassignment of the compensation values, and the compensation values are then again reassigned to the adjacent magnetic field detectors. The stored measured values are then corrected with the reassigned compensation values, and the measured values obtained with the maximum compensation values before and after the reassignment are compared with one another. In the case of a reduction in the corrected measured values on the basis of the reassignment of the compensation values, the compensation values are again assigned to the adjacent magnetic field detectors, and if the threshold values fall short of the assignment of the compensation values to the magnetic field detectors, the measured values are retained. With this measure, an adjustment of the compensation values is achieved in accordance with the direction of the position change between the weld and the magnetic field detectors.

The device according to the invention is arranged such that the magnetic field detectors are each connected by a detection and coding circuit with a first memory connected in the manner of a shift register, with a second memory and with a subtracter, the other inputs of which are connectable to the outputs of the detection and coding circuit or those of the second memory as desired. A threshold value detector is connected behind the subtracter, the detector being settable to positive and negative threshold values and being connected to a compensation control circuit by which the shift in the stored values in the first memory, the readout of the first and second memories, the application of the inputs of the subtracter to the outputs of the detection and coding circuit or the second memory, and the transmission of the result of the comparison to a connected evaluation unit are controllable.

With this device, it is possible in a simple manner and with great speed both to adapt the compensation values to the respective position between the weld and the magnetic field detectors, to obtain the corrected measured values corresponding to the respective position and to weight the values for later processing. The subtracter, the comparator and the compensation control circuit are preferably realized by a microprocessor, by which the input into the second memory of the inquiry of the magnetic field detectors and the time-division multiplex conversion of the output signals of the magnetic field detectors into digital signals can be controlled.

It is practical to have the output of the first memory fed back to the input. This arrangement permits the number of memory positions to be adapted to the number of magnetic field detectors. The memory capacity requirement is therefore adaptable to the prevailing conditions of the test device.

BRIEF DESCRIPTION OF THE DRAWINGS

The invention is described in more detail in the following with the aid iof a typical embodiment illustrated in the drawings, of which:

FIG. 1 is a perspective view of a device in accordance with the present invention for non-destructive testing of ferro-magnetic bodies, FIG. 2 is the arrangement shown in FIG. 1 seen from the front, FIG. 3 shows details of the rows of magnetic field detectors shown in FIG. 1, as seen from the front.

DETAILED DESCRIPTION OF THE PREFERRED EMBODIMENTS

A device for non-destructive testing of ferro-magnetic pipes 1, of which one is shown in FIGS. 1 and 2, contains a magnetization system of two pairs of magnets 2, 3 which are arranged one behind the other in the longitudinal direction of the pipe 1. The pair of magnets 2 contains a first magnetic pole shoe 4, whose end facing the pipe is for example a magnetic north pole, and a second magnetic pole shoe 5, which has a magnetic pole opposite to that of the first pole shoe 4 at its end facing the pipe 1. The magnetic pole shoes 4, 5, are arranged along the same central axis 6. Similarly, the pair of magnets 3 also comprises two magnetic pole shoes 7, 8, with pole shoe 7 having a magnetic north pole at its end facing the pipe 1 and the pole shoe 8 having a magnetic south pole at its end adjacent to the pipe 1. The magnetic pole shoes 7, 8 are also arranged along a common central axis 9.

While the magnet pairs 2 and 3 are attached in a stationary manner, the pipe 1 is moved in the direction of its longitudinal axis 10 between the magnetic pole shoes 4, 5, 7 and 8 during the test. Two magnetic fields are aligned on the pipe 1 through the magnetic pole shoes 4, 5, 7 and 8. The central axes of these magnetic fields correspond with the central axes 6 and 9, respectively, of the magnetic pole shoes 4, 5 and 7, 8. The central axes 6 and 9 are inclined with respect to one another at an angle corresponding to the quotient of one hundred and eighty degrees and the number of the magnetic fields aligned on the pipe 1. Since two magnetic fields are aligned on the pipe 1, in FIG. 1 the angle $\alpha$ is ninety degrees. Thus, the field lines of the magnetic fields run predominantly in the pipe walls in the inside of the pipe, and the magnetic fields are dimensioned sufficiently to magnetically saturate the pipe walls.

The magnetic resistance is greatly increased by cracks, shrinkage cavities or holes in the pipe walls. Part of the magnetic field does not close over the cracks, cavities or holes, but instead the magnetic field closes over the air gap outside the outer or inner pipe surface. This part of the magnetic field is picked up by the magnetic field detectors. Measurement of a field of this nature running outside the surface of the pipe thus indicates a material fault or a structural fault in the walls of the pipe 1.

Between the pole shoes 4, 5 and 7, 8 directing the magnetic fields onto the pipe 1, rows 12 and 13 of magnetic field detectors are arranged along the surface of the pipe 1. Rows 12, 13 are located a short distance from the surface of the pipe 1. As shown in FIGS. 1 and 2, the rows 12 and 13 are arranged close to the outside walls of the pipe 1. Rows of magnetic field detectors can also be arranged inside the pipe 1, the rows extending along the inner surface.

Rows 12, 13 cover in the pipe 1 a test zone extending in the axial direction 10 and having a width corresponding to the length of the respective row 12 or 13. Rows 12, 13 are, like the pairs of magnets 2, 3, arranged in a stationary manner. The two rows 12 and the two rows 13 each cover two zones on the surface of the pipe 1, each zone enclosing an angle $\beta$ which is calculated by dividing one hundred and eighty degrees by the number of magnetic poles. Each row 12, 13 shown in FIGS. 1 and 2 thus encloses at least an angle of 45°. Rows 12, 13 can also be made longer such that angle $\beta$ is larger than 45°. With the rows 12, 13 in the sizes shown in FIGS. 1 and 2, however, pipe 1 can be tested over its entire periphery.

If a testing device is required with which the pipe 1 is not to be tested over its entire periphery, but only over a part of it, corresponding for example to the width of a weld 16 plus its tolerance zone, a row of magnetic field detectors can be provided which is only as wide as the required periphery zone. In an extreme case the use of only one pair of magnets could suffice in this instance. The testing device shown in FIGS. 1 and 2 thus has circuitry permitting it to test not just a part of the periphery, but the whole periphery as well.

Hall generators are provided as magnetic field detectors in rows 12, 13 to which are transmitted pulse sequences as control currents. The outputs of the Hall generators are applied in a time-division multiplexing manner to an evaluation circuit described below. The time-division multiplex inquiry of a number of N Hall generators is synchronized with the pulse sequences of the control currents.

In rows 12, 13, Hall generators 15 can be arranged in varying alignment with the surface of the pipe 1. The Hall generators 15 are arranged, in the embodiment shown in FIG. 3, with their broad sides 19 perpendicular to the opposite surface element of the pipe 1. As shown, the Hall generators 15 are arranged in two layers 20, 21 one above the other. The use of the respective layer 20, 21 for error testing depends on the selection criteria of the errors. The embodiment shown in FIG. 3 permits dense packing of the Hall generators next to one another. This enables easier location of errors in the structure of pipe 1.

Figure 4:
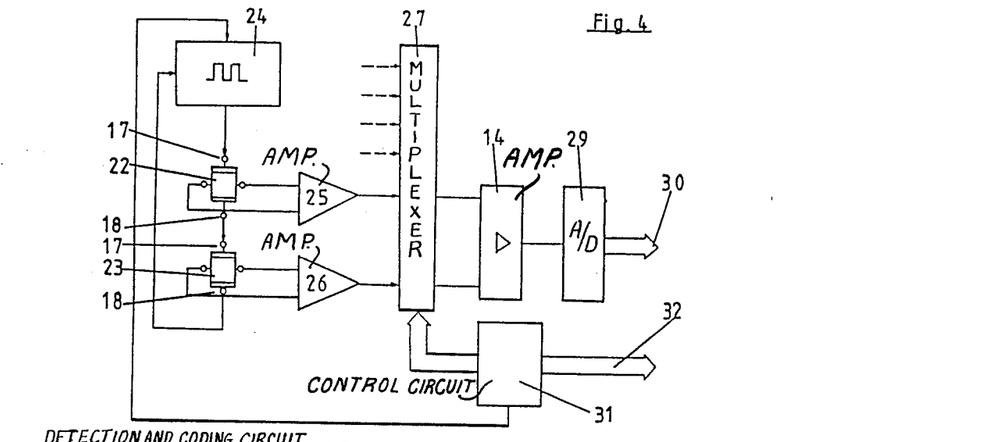
FIG. 4 is a block diagram of a first portion of a measured value processing circuit connected with magnetic field detectors.
Figure 6:
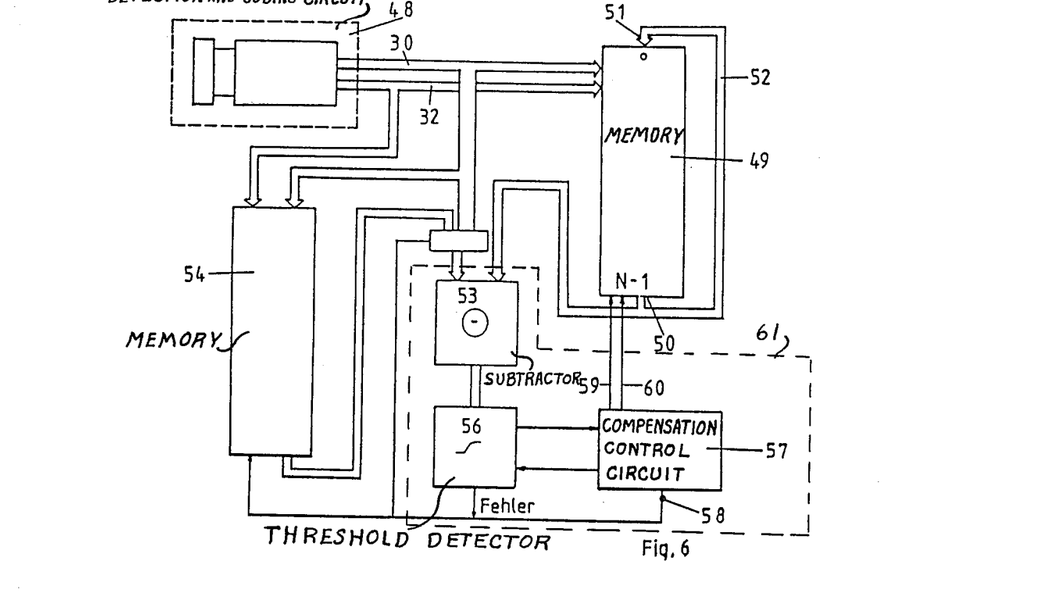
FIG. 6 is a block diagram of a second portion of a measured value evaluation circuit connected to the first part of the circuit.

The Hall generators may also be arranged as shown in FIGS. 4 and 6 of DE-PS No. 3132808.

In FIG. 4, for example two Hall generators 22, 23 with their connecting electrodes 17, 18 are shown. Rows 12, 13 are formed of Hall generators of the arrangement 15 as shown in FIG. 3. The type of the connection of all adjacent paired generators 15 in one of the positions 20, 21 corresponds to that of the two Hall generators 22, 23. The electrodes supplying the control current are connected in series in the case of the Hall generators 22, 23. A constant current generator 24 supplies the electrodes with the control current. As shown in FIG. 4, the electrodes which receive the Hall voltage are connected to an input of an amplifier 25 or 26 in the case of the Hall generators 22, 23.

The constant current generator 24 produces a pulse sequence with a pulse-interval-to-pulse-length ratio of 1:10. The thermal load is reduced by the pulse loading of the Hall generators 22, 23. Higher control current amplitudes can therefore be applied. Since the Hall voltage is proportional to the control currents, there are sufficiently high Hall voltages even with small magnetic fields. An increase of the parameters of the Hall generators 22, 23 thus results. It is therefore possible to use inexpensive sensors as Hall generators 22, 23 which are normally used for pickup of magnet positions. The pulsed application to the Hall generators 22, 23 of control currents also permits the monitoring of selected values in the pulse intervals. It is thus possible to determine the temperature-dependent zero point constancy of the Hall generators 22, 23 in the pulse intervals and to stipulate the correction amounts corresponding to the temperature values with which the measured values are corrected in order to eliminate the effects of temperature changes.

The outputs of the amplifiers 25, 26 are connected to the inputs of a multiplexor 27, the amplifiers fed by the other Hall generators 15 also being connected to the inputs but not being illustrated in detail. The multiplexer 27 is connected by its outputs, to which the analog signals emitted by the amplifiers 25, 26 or by the other amplifiers not illustrated are transmitted, to inputs of an amplifier 14. Amplifier 14 is connected to an analog-digital converter 29, the outputs 30 of which represent the digitalized measured values of the Hall generators 22, 23. A control circuit 31 synchronizes the control current pulses of the constant current generator 24 in alignment with the addresses applied to the multiplexer 27, the addresses connecting the Hall generators 22, 23 respectively through to the amplifier 14. The addresses for identification of the hall generator 22, 23 selected are available at output 32 of the control circuit 31.

Figure 5:
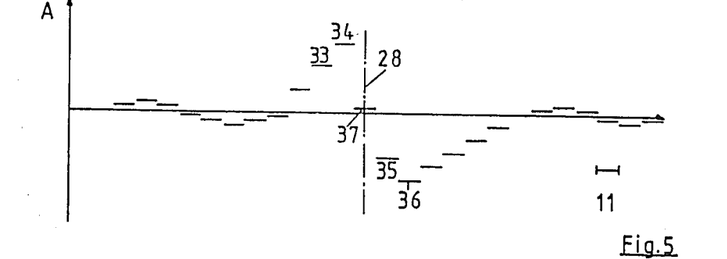
FIG. 5 is a diagram of the compensation quantities necessary along a circular peripheral line of a pipe for suppressing the stray flux of the weld as a function of the distance from the weld.

FIG. 5 shows the measured values caused by the weld 16 when arranged in a relative position to the magnetic field detectors as a result of stray fluxes in the Hall generators 15. The path on the pipe 1 is shown along the abscissa. The path represents at least a part of an arc of a circle resulting from a cross-section through the pipe 1. The stray flux measured values obtained at the respective points are shown in the ordinate direction, the precondition being that there are no structural faults apart from the weld in the pipe 1 at the points at which the measured values shown in FIG. 1 were obtained. The measured values shown in FIG. 5 can be established on a test specimen or on a fault-free point of a pipe 1 to be tested, and these values can be used as compensation values in the further course of testing of the pipes 1 of identical shape and size in order to compensate the values generated by the respective magnetic field detectors towards a minimum, possibly to zero, assuming there are no structural faults. The measured values shown in FIG. 5 are generated in Hall generators 15 arranged next to one another along the circular generating line. The measured values run approximately symmetrical to the centerline 28 of the weld 16. Some of the measured values 33, 34, 35, 36 are identified in FIG. 5 for more detailed explanation of the method. Measured values 34, 36 are maximum values. A unit of travel 11 is also shown in FIG. 5 corresponding to the section assigned to a Hall generator 15 on the surface of the pipe 1 running perpendicular to the longitudinal axis 10.

The pipe 1 is guided in a certain angular position in the longitudinal direction by a device comprising the pairs iof magnets 2, 3 and the rows of magnetic field detectors 12, 13 as shown in FIG. 1. The guiding device (not illustrated in detail) of the pipe 1 prevents unacceptably large changes in the originally set angular position of the weld. Certain lateral changes in the position of the magnetic field detectors with regard to the weld as a result of rotational movements of the pipe 1 during conveying in the longitudinal direction cannot be avoided without unacceptable expense. The occurrence of the measured values illustrated in FIG. 5, e.g., of measured values 33 to 36 in the Hall generators 15, depends on the angular position of the weld 16. Measured values 33, 34, and 35, 36 occur for example in the adjacent Hall generators 15. A further value 37 results in that particular Hall generator which is located above the centerline 28 of the weld 16. One each of the measured values illustrated in FIG. 5 is therefore assigned to a certain Hall generator as a function of the angular position of the weld 16.

An address generated by the control circuit 31 corresponds to the particular Hall generator. The measured values in accordance with FIG. 5 are stored after pickup in a clear assignment to the Hall generators 15. The assignment is best performed by means of storage in cells of a memory determined by a preset sequence. During testing of the pipe 1 for structural faults, the measured values shown in FIG. 5 are used as compensation values to detect structural faults near to or in the weld 16. The compensation values and the measured values obtained in the test are offset against one another with the correct sign for the respective Hall generator 15. This means that the measured values 33, 34 referred to in the following as compensation values are subtracted from the measured values of the respective Hall generators 15, while the measured values 35, 36, which are also compensation values, are added up to the measured values of the corresponding Hall generators 15. The addressing of the multiplexer 27 and the inquiry entailed of the Hall generators 15 electronically simulates the rotation of a magnetic probe, and the sequence of inquiries of the Hall generators 15 can take place very quickly through the use of electronic switching elements. This simulates a "rotation speed" that is considerably higher than the speeds of rotatable magnetic probes achievable economically with mechanical means.

The subtraction of the compensation values 33 to 37 and of the other compensation values not discussed but shown in FIG. 5 result in corrected measuring values from which the influence of the weld 16 has been largely eliminated. These corrected measured values are then subjected to a further test. They are checked for the presence of structural faults using predetermined threshold values. The measured values of all Hall generators 15 can be weighted with the same reference thresholds. This identical weighting is possible because the compensation by subtraction is a linear process and because no dynamic problems can occur due to digitalization.

Exact adherence to the respective angular position of the weld 16 during longitudinal displacement of the pipe 1 is uneconomical on account of the extremely high structural expense entailed. Accordingly, it is possible for angular movements of the pipe 1 to occur during the longitudinal displacement. These angular movements change the positions of the Hall generators 15 in relation to the weld 16. To be able to correct the influence of the weld on the measuring values even when the angular position of the weld 16 changes in the course of the longitudinal movement, the change in the angular position is monitored. The compensation values 33 to 37 and the other compensation values shown in FIG. 5 and not identified in detail are reassigned to the respective Hall generators 15 in accordance with this change in the angular position of the weld 16. The measured values are corrected using the reassigned compensation values before further processing takes place on the basis of the threshold values.

The change in the rotational angle of the weld 16 during longitudinal displacement of the pipe 1 is detected in the following manner. Not only the corrected measured values are determined as to their position outside the threshold values, but also the mathematical signs of the measured values at which the overstepping of the threshold values occurs. The indications of threshold values having been overstepped are initially evaluated not as a sign of structural faults in the material of pipe 1, but as a sign of a change in the angular position of the weld 16. This is shown clearly in FIGS. 7a–7c.

Figure 7A:
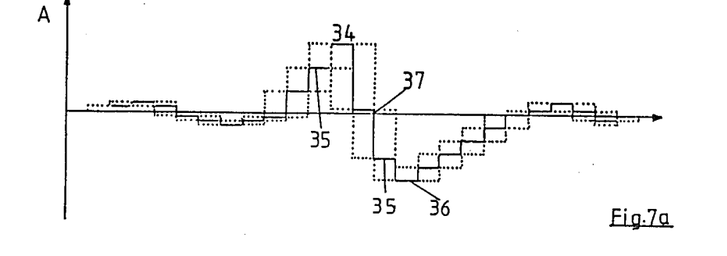
FIGS. 7a-c are diagrams of the various compensation quantities assigned to magnetic field detectors as a function of the respective positions of the magnetic field detectors on the periphery of the body to be tested.

The compensation values 33 to 37 and other compensation values not identified for a given angular position of the pipe 1 are shown again in FIG. 7a. When testing the pipe 1, the measured values picked up with the Hall generators 15 are offset against the compensation values in the assignment arrangement given in FIG. 7a. If no structural faults are present, the measured values are approximately the same size as the compensation values. The result of subtracting the compensation values from the measured values is therefore a minimum amount of around zero. As long as no faults are indicated by corrected measured values outside the threshold values, the assignment of the compensation values to the Hall generators 15 is retained.

Let it be assumed, however, that the angular position of the weld 16 has changed by a travel unit 11 during the longitudinal movement of the pipe 1, the change corresponding to the travel unit 11 assigned to a Hall generator 15 on the periphery transverse to the longitudinal axis 10. The correction of the measured values generated by the Hall generators 15 is first performed with the compensation values shown by the unbroken line in FIG. 7a. The recorded measured values correspond however to a lateral shift of the Hall generators 15 to the left with relation to the weld 16 by the position of one Hall generator 15.

The result of this is that measured values occur—unless no structural faults are present—that are represented in FIG. 7a with dotted lines. The compensation values 33 to 37 and the compensation values not identified are subtracted from these measured values. The result is the corrected measured values shown in FIG.

Figure 7B:
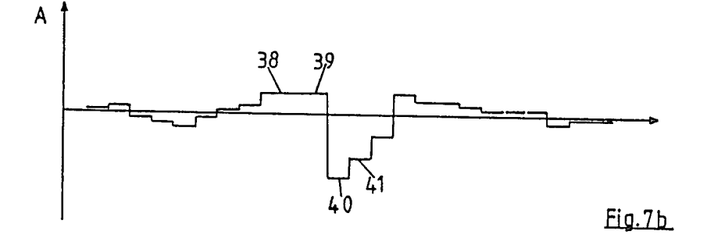

7b, a large number of which exceed the given threshold values. An error signal is therefore generated. Some of the corrected measured values exceeding the preset threshold values are numbered 38, 39, 40, 41 in FIG. 7b. At the same time the exceeding of the threshold values is established, the sign for the corrected measured value, e.g. 38 to 41, is established for the respective Hall generator 15. An angular rotation of the weld 16 in a certain direction, e.g. to the left, corresponds to a certain sign prefixing the corrected measured values. If, for instance, the sign of the corrected measured values was negative and a positive sign was established for the subsequently obtained measured values following correction with the new compensation amounts, than an angular rotation to the left has taken place. This instance is illustrated in FIG. 7b. The compensation values are reassigned after the change in the angular position of the weld has been established.

This new reassignment requires for the instance shown in FIG. 7b that the compensation values be shifted to the left by the position of 1 Hall generator 15, i.e., the compensation values of the Hall generators 15 are assigned to the Hall generators adjacent to them on the left-hand side. After reassignment of the compensation values, the original measured values are again corrected and then compared with the corrected measured values determined beforehand and checked for whether they exceed the predetermined thresholds. If the second corrected measured values obtained with the new compensation values are lower than the first corrected measured values, a further reassignment of adjacent compensation values can be performed in the same direction. This results in third corrected measured values, which are compared with the second corrected measured values. If the third corrected measured values are higher than the second ones, then the compensation value assignments for the second corrected measured values apply. If, however, some or all of the second measured values still overstep the predetermined threshold, there is a fault. On the other hand, if the third corrected measured values are lower than the second ones, the compensation values are reassigned. Fourth corrected measured values are then created and compared with the previously established corrected measured values until the last-obtained corrected measured values are higher than the previously determined measured values.

Figure 7C:
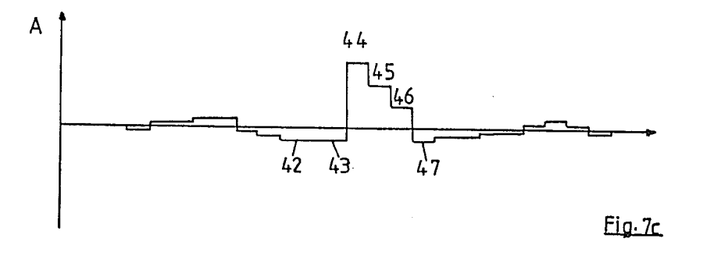

In the event of a change in the angular position of the weld 16 by one travel unit 11 to the right, the measured values shown as a dotted line in FIG. 7a are an example of the result, the measured values being corrected by compensation values 33 to 37 and by the compensation values not identified. The result of this correction is shown in FIG. 7c. The corrected values 42, 43, 44, 45, 46, 47 occur, for example, outside the ranges determined by the preset threshold values. A displacement of the weld 16 to the right corresponds to a negative sign at those points on the periphery whose Hall generators 15 have triggered corrected values with positive signs or with the value zero. After determination of the threshold value overruns and the signs connected therewith, the compensation values are reassigned. This reassignment entails in the instance shown in FIG. 7c the compensation values being displaced to the right by one position of a Hall generator 15, i.e., the compensation value of each Hall generator is assigned to the Hall generator adjacent to it on the right. After reassignment of the compensation values, the original measured values are recorrected, and compared with the previously obtained corrected measured values and checked for whether the given thresholds are exceeded.

Since a change in the angular position of the weld 16 once initiated can have a tendency to increase, a further measure as described in detail below is also useful.

A further "displacement" of the compensation values takes place in the direction determined by the signs of the corrected measured values 38 to 41 or 42 to 47. The compensation values of the Hall generators 15 are, depending on the sign, assigned either to the adjacent right-hand or left-hand Hall generator 15. The maximum compensation values 34, 36 are then subtracted from the stored measured values. The resultant corrected measured values are compared with the corrected measured values obtained before the reassignment. If the corrected measured values obtained after the reassignment of the compensation values are lower than those determined before the reassignment, then the second compensation must be retained if the threshold values are not reached. If, however, the corrected measured values obtained after the reassignment are higher, then the reassignment must be revoked. This method is continued until the minimum corrected measured values are obtained by the assignment of suitable compensation values for the respective magnetic field detectors. The arrangement therefore seeks the correlation optimum, i.e., the minimum indication amount between measured value set and compensation value set.

A device for performing the procedural steps described above is shown in FIG. 6. The device in accordance with FIG. 6 contains the portion shown in FIG. 4, identified with reference numeral 48 and functioning as a detection and coding circuit.

As shown in FIG. 6, a first memory 49 is connected to the outputs 30 for recording the sample compensation values, and output 50 of the first memory is fed back to the inputs 51 of the first memory via the leads 52. The memory 49 is a RAM, i.e., a random access memory. One memory, mode HM-6512 made by Harris, is suitable for 64 magnetic field detectors. Such a memory has a capacity of 64 values of 12 Bits each. The outputs 30 are also connected to one input of a subtracter 53, whose other input is connectable to the outputs 50 of the memory 49. The subtracter 53 thus has two different inputs, each of which can comprise several points for parallel input of values. In addition, a second random access memory 54 can be connected to the outputs 30 as a buffer for the measured value packages. The output 55 of the memory 54 is optionally connectable to the input of the subtracter 53.

As also shown in FIG. 6, the outputs 32 are connected to the addressing circuits of memories 49 and 54. In addition, a threshold value detector 56 is connected to the output of the subtracter 53, the detector being set to either a positive or to a negative value. The threshold values establish the limits sufficient for the detection of a structural fault. If any threshold value is exceeded, the threshold value detector 56 emits an error signal at its output. A compensation control circuit 57, connected to the threshold value detector 56, receives its input from the threshold value detector 56.

The compensation control circuit 57 also influences the release of the error indication of the threshold value detector 56. Furthermore, the compensation control circuit 57 has an output 58 for controlling the readout of the contents of memory 54 and for switching the input of the subtracter from the outputs 30 to the outputs 55.

Two further outputs 59, 60 of the compensation control circuit 57 are connected to the memory 49. Outputs 59, 60 control the displacement of the contents of the memory 49 in one direction each. The synchronization between the time-division multiplex inquiry of the Hall generators and the compensation control circuit 57 takes place via the addresses assigned to the Hall generators. The subtractor 53, the threshold value detector 56 and the compensation control circuit 57 are preferably realized by a microprocessor 61, as shown by hatched lines in FIG. 6.

The compensation values in memory 49 are stored under addresses assigned to the respective Hall generators 15. When the compensation values are being read in, the outputs 30 feed the measured values obtained from a test specimen into the memory 49. If the compensation values are available in memory 49, the outputs 32 control the readout of the compensation values during feed of the measured values to the subtracter 53, in which the difference between the respective measured value of a Hall generator 15 and the compensation value assigned to it is formed. The corrected measured values pass to the threshold value detector 56, whose output signal is monitored by the compensation control circuit 57. If the given limits are not exceeded, the compensation control circuit 57 does not intervene in the processing sequence of the measured values. Then the measured values do not pass to the subtracter 53, but to the memory 54, so that the measured values are still available for any correction becoming necessary.

If the threshold value detector 56 signals that one or both of the threshold values has been exceeded, the compensation control circuit 57 checks on the basis of the sign prefixing the corrected values the direction in which a displacement of the contents of the memory 49 is necessary compensation control circuit 57 then and gives the appropriate instruction via one of the outputs 59, 60 to the memory 49, and the contents of the memory cells are each displaced by one memory cell. The memory 49 therefore functions in the manner of a shift register whose contents can be shifted in either direction. The compensation control circuit 57 then initiates readout of the measured values from memory 54, supplies the measured values to the subtracter 53 and forms the difference between the measured values and the compensation values. The measured values corrected in this manner pass in their turn to the threshold value detector, where they are again checked. The maximum values of the quantity integral with a prefixed sign are first stored on the basis of the number of measured values and of the absolute measured values. The compensation control circuit 57 then initiates a further displacement of the contents in memory 49 by one memory cell in the previously determined direction.

With the compensation values reassigned in this manner, new corrected measured values are obtained on the basis of the contents of memory 54. The maximum corrected measured values and the quantity integral are for comparison with the maximum corrected measured values in accordance with the previously conducted shift operation in memory 49. If the values are lower, the last shift operation is retained, otherwise the last shift operation in memory 49 is revoked. The corrected measured values are checked in the threshold value detector for structural faults, if necessary, by setting new threshold values.

The circuit seeks the optimum correlation between the measured value and compensation value sets. This is generally expressed by a minimum in the integral of the indicated values. This can be approximately zero is an instance where there are no faults. If an error occurs in the signal, this signal also remains as a minimum value above the given threshold, since the minimum is correspondingly far removed from the fault-free ideal case by the error. The search for the minimum results in a stable control loop, since the operation is broken off as soon as the signal is below the threshold of the threshold value detector 56. This prevents the system from "hunting" as a result of noise signals.

I claim:

1. A method for non-destructive testing of a ferromagnetic body for structural defects by means of magnetizing the body, the structural defects causing changes in the magnetic field pattern which changes are picked up by stationary magnetic field detectors arranged on or near the surface of said body, said detectors being arranged along the periphery of the body and having outputs connected in a specified sequence and in a time-division multiplex manner for evaluation, comprising the steps of:
   (a) determining compensation values as a function of the positions of the respective magnetic field detectors with respect to a reference position of a weld of a test specimen, said compensation values being used to minimize measured values obtained in the measurement of the test specimen in the reference position of the weld, said test specimen not having any structural defects;
   (b) determining during measurement of a specimen which is to be tested for structural defects the extent of lateral changes in the position of the specimen being tested with respect to the magnetic field detectors when the weld is deflected from the reference position;
   (c) reassigning the compensation values in accordance with the changes in the position of the weld of the specimen being tested such that the difference between the measured values of the specimen being tested and the compensation values is minimized;
   (d) subtracting the compensation values from the measured values of the specimen being tested to obtain corrected measured values which approach zero; and
   (e) testing the corrected measured values for the presence of structural defects by comparing the corrected measured values to predetermined threshold values.

2. A method as defined in claim 1, wherein said steps (c) through (e) comprise the further steps of:
   (f) storing the measured values produced by the magnetic field detectors when testing the specimen for structural defects so that lateral changes in the position of the respective weld in relation to the magnetic field detectors can be monitored;
   (g) subtracting the compensation values obtained in the measurement of said test specimen not having any structural defects from the measured values of the specimen being tested to obtain first corrected measured values which approach zero;
   (h) checking the first corrected measured values for whether they exceed the predetermined threshold values and for their signs as well as for the value of a quantity integral of all measured values;
   (i) when the predetermined threshold values are exceeded, reassigning the compensation values for the respective magnetic field detectors to the compensation value of an adjacent magnetic field detector as a function of sign changes in the first corrected measured values;

(j) subtracting the reassigned compensation values from the measured values of the specimen being tested to obtain second corrected measured values;

(k) comparing the second corrected measured values with the first corrected measured values;

(l) when the second corrected measured values are lower than the first corrected measured values, repeating said steps (h)-(k) with reassigned compensation values of another adjacent magnetic field detector until present corrected measured values exceed the previous corrected measured values obtained in the previous sequence of steps (h)-(k);

(m) assigning the reassigned compensation values to the previous corrected measured values as the lowest corrected measured values for further compensation;

(n) checking the lowest corrected measured values obtained as to whether they exceed the threshold values; and (o) signalling errors when the threshold values are exceeded.

3. A method as defined in claim 1, comprising the further steps of:

(p) storing the measured values of the specimen being tested which are corrected by compensation values having the greatest absolute value and the quantity integral at every reassignment of the compensation values;

(q) again reassigning the compensation values to respective adjacent magnetic field detectors;

(r) correcting said stored measured values using the again reassigned compensation values by comparing with one another the measured values corrected with the compensation values having the greatest absolute value which were obtained before and after the reassignment;

(s) when the corrected measured values are smaller due to the reassignment of the compensation values, again reassigning the compensation values to adjacent magnetic field detectors; and (t) when the threshold values are not exceeded by the corrected measured values, retaining the last assignment of the compensation values for the magnetic field detectors.

4. Device for non-destructive testing of a ferromagnetic body for structural defects by means of magnetizing the body, the structural defects causing changes in the magnetic field pattern which changes are picked up by stationary magnetic field detectors arranged on or near the surface of said body, said detectors being arranged along the periphery of the body and having outputs connected in a specified sequence and in a time-division multiplex manner for evaluation, the device including:

a detection and coding circuit responsive to said magnetic field detectors for detecting and coding said magnetic field pattern during testing of a specimen having a weld in order to determine the extent of lateral changes in the position of the specimen with respect to the magnetic field detectors when the weld is deflected from a reference position;

a first memory connected via said detection and coding circuit to each of the magnetic field detectors, said first memory storing compensation values determined as a function of the positions of the respective magnetic field detectors with respect to the weld of a test specimen in the reference position, said compensation values being used to minimize measured values obtained in the measurement of the test specimen in the reference position of the weld, said test specimen not having any structural defects, and said first memory operating as a shift register;

a second memory connected via said detection and coding circuit to each of the magnetic field detectors, said memory functioning as a buffer memory;

a subtractor having a first input connected alternatively to outputs of the detection and coding circuit and the second memory and a second input connected to an output of said first memory for subtracting the compensation values from measured values of the specimen being tested to obtain corrected measured values which approach zero;

a threshold value detector settable to negative and positive threshold values, said threshold value detector comparing the output of said subtractor with predetermined threshold values; and a compensation control circuit which outputs a control signal for shifting the compensation values stored in the first memory in accordance with the changes in the position of the weld of the specimen being tested such that the difference between measured values of the specimen being tested and the shifted compensation values is minimized; for reading the first and second memories; for selectively applying to said first input of the subtractor either the outputs of the detection and coding circuit or an output of the second memory; and for outputting the result of the comparison with said predetermined threshold values for further evaluation.

5. A device as claimed in claim 4, wherein the output of the first memory is fed back to its input.

6. A device as claimed in claim 4, wherein the first and second memories are random access memories.

7. A device as claimed in claim 4, wherein a shift of the contents of adjacent memory cells of the first memory is optionally controlled in two directions by the compensation control circuit.

8. A device as claimed in claim 4, wherein the subtractor, the threshold value detector and the compensation control circuit functions are performed by a microprocessor.

* * * * *